(12) United States Patent
Hansen

(10) Patent No.: US 6,669,980 B2
(45) Date of Patent: Dec. 30, 2003

(54) METHOD FOR SPRAY-COATING MEDICAL DEVICES

(75) Inventor: Henrik Hansen, Co Galway (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/954,579

(22) Filed: Sep. 18, 2001

(65) Prior Publication Data

US 2003/0054090 A1 Mar. 20, 2003

(51) Int. Cl.[7] .............................. B05D 1/04; A61L 27/00
(52) U.S. Cl. ...................... 427/2.24; 427/2.1; 427/2.25; 427/2.26; 427/2.28; 427/2.3; 427/2.31; 427/458; 427/475; 427/421
(58) Field of Search ................................ 427/2.1, 2.24, 427/2.25, 2.26, 2.28, 2.3, 2.31, 458, 475, 421

(56) References Cited

U.S. PATENT DOCUMENTS

| | | | | |
|---|---|---|---|---|
| 4,505,957 A | * | 3/1985 | Cobbs et al. | 427/422 |
| 4,749,125 A | * | 6/1988 | Escallon et al. | 239/3 |
| 6,355,058 B1 | * | 3/2002 | Pacetti et al. | 623/1.15 |
| 6,364,903 B2 | * | 4/2002 | Tseng et al. | 623/1.15 |
| 6,368,658 B1 | * | 4/2002 | Schwarz et al. | 427/2.15 |

OTHER PUBLICATIONS

Web pages retrieved from the Internet on Apr. 10, 2001 at <URL: www.terronics.com> that describe Terronics' spray nozzle.

* cited by examiner

Primary Examiner—Shrive P. Beck
Assistant Examiner—Jennifer Kolb Michener
(74) Attorney, Agent, or Firm—Pennie & Edmonds LLP

(57) ABSTRACT

A method for spray-coating a medical device by using a nozzle apparatus having a chamber that is connected to at least one opening for dispensing a coating formulation. Such method comprises (a) grounding the surface of the medical device that is to be coated and (b) applying a coating formulation, which comprises a polymeric material and a solvent, by (1) providing the nozzle apparatus comprising a chamber connected to at least one opening for dispensing the coating formulation; (2) placing the coating formulation into the chamber; (3) electrically charging the coating formulation; (4) creating droplets of the electrically charged coating formulation; and (5) depositing the droplets of coating formulation onto the grounded surface to form a coating on the surface.

16 Claims, 4 Drawing Sheets

METHOD FOR SPRAY-COATING MEDICAL DEVICES

FIELD OF THE INVENTION

The invention relates generally to a method for coating a medical device. More particularly, the invention is directed to a method for spray-coating a medical device with an electrically charged coating formulation.

BACKGROUND OF THE INVENTION

There are various medical devices for long-term treatment of a patient that are designed to function as permanent implants. One example of such medical devices is an implantable stent. During a surgical or invasive procedure, the medical practitioner inserts or implants a stent into a blood vessel, the urinary tract or other body lumina that are difficult to access for the purpose of, inter alia, preventing restenosis, providing vessel or lumen wall support or reinforcement and applying therapeutic treatments. Such uses of stents for long-term treatment are common. Typically, such prostheses are applied to the location of interest by using a vascular catheter, or similar transluminal device, to position the stent at the location of interest where the stent is thereafter expanded. These medical devices designed as permanent implants may become incorporated in the vascular or other tissue that they contact.

However, the implantation of a medical device into the body of a patient can cause the body tissue to exhibit adverse physiological reactions. For instance, the insertion or implantation of certain catheters or stents can lead to the formation of emboli or clots in blood vessels. Similarly, the implantation of urinary catheters can cause infections, particularly in the urinary tract. Other adverse reactions to medical devices include cell proliferation which can lead to hyperplasia, occlusion of blood vessels, platelet aggregation, rejection of artificial organs, and calcification.

To reduce such adverse effects as well as for other benefits, a medical device can be coated with a coating comprising a biocompatible polymer. Also, the coating can incorporate a biologically active or bioactive material. A medical device coated with such a coating can be used for direct administration of a biologically active material into a particular part of the body when a disease is localized to the particular part, such as, without limitation, a body lumen including a blood vessel, for the treatment of the disease. Such direct administration may be more preferred than systemic administration. Systemic administration requires larger amounts and/or higher concentrations of the biologically active materials because of inefficiencies associated with the indirect delivery of such materials to the afflicted area. Also, systemic administration may cause side effects which may not be a problem when the biologically active material is locally administered.

For example, implanted stents have been used to carry medicinal agents, such as thrombolytic agents. U.S. Pat. No. 6,099,562 to Ding et al. discloses a medical device having an undercoat containing a biologically active material covered by a topcoat substantially free of pores, and U.S. Pat. No. 5,879,697 to Ding et al. discloses a coated medical device wherein the coating contains a reservoir layer containing a biologically active material. Pinchuk, in U.S. Pat. No. 5,092,877, discloses a stent of a polymeric material which may have a coating associated with the delivery of drugs. A patent to Sahatjian, U.S. Pat. No. 5,304,121, discloses a coating applied to a stent consisting of a hydrogel polymer and a pre-selected drug such as a cell growth inhibitors or heparin.

Thus, a number of various coatings for medical devices have been used. Such coatings have been applied to the surface of a medical device mostly by either spray-coating or dip-coating the device with a coating solution. The spray-coating method has been frequently used because of its excellent features, e.g., good efficiency and control over the amount or thickness of coating. However, the conventional spray-coating methods, which are usually implemented with a device such as an airbrush, have drawbacks. For example, when a medical device has a structure such that a portion of the device obstructs sprayed droplets from reaching another portion of the device, then the coating becomes uneven. Specifically, when a spray-coating is employed to coat a stent having a tube-like structure with openings, such as stents described in U.S. Pat. Nos. 4,655,771 and 4,954,126 to Wallsten, the coating on the inner wall of the tube-like structure tends to be thinner than that applied to the outer wall of the tube-like structure. Hence, conventional spraying methods tend to produce coated stents with coatings that are not uniform.

Furthermore, conventional spraying methods are inefficient. In particular, generally only 5% of the coating solution that is sprayed to coat the medical device is actually deposited on the surface of the medical device. The majority of the sprayed coating solution is therefore wasted.

Besides conventional spray-coating methods, electrostatic deposition methods have been suggested for coating medical devices. For instance, U.S. Pat. Nos. 5,824,049 and 6,096,070 to Ragheb et al. mention the use of electrostatic deposition to coat a medical device with a bioactive material. In the conventional electrodeposition or electrostatic spraying method, a surface of the medical device is grounded and a gas is used to atomize the coating solution into droplets. The droplets are then electrically charged using, for example, corona discharge, i.e., the atomized droplets are electrically charged by passing through a corona field. Since the droplets are charged, when they are applied to the surface of the medical device, they will be attracted to the surface since it is grounded.

However, one disadvantage of conventional electrostatic spraying is that it requires at least two (2) input sources for the spraying apparatus in order to apply the coating formulation to the surface of a medical device in addition to an input source for providing the coating formulation. First, one input source is required for the gas that is used to atomize or form the droplets of coating formulation. Also, a second input source is needed for the static electricity source that is used to charge the droplets. The need for two additional separate input sources complicates this spraying method.

Another disadvantage is that since the gas pressure creates the droplets and moves or propels the droplets to the target, the control of the gas pressure is crucial for achieving a good coating. However, it is not easy to control the gas pressure so that the target surface is evenly and sufficiently coated without losing much of the coating solution.

Therefore, there is a need for an improved method for coating medical devices that provides very even or uniform coatings over the entire surface that is to be coated. Also, there is a need for more efficient methods of spray-coating a medical device where a greater amount of coating formulation that is sprayed is actually deposited on the surface of the medical device. In addition there is a need for a more simplified method for spray-coating the surface of a medical device.

Each of the references cited herein is incorporated by reference herein.

SUMMARY OF THE INVENTION

This and other objectives are accomplished by the present invention. To achieve these objectives, I have developed a method which is efficient and highly controlled to realize a very uniform coating on even a medical device having intricate surfaces. Specifically, in the method of the present invention, the surface to be coated is grounded. A coating formulation, which comprises a polymeric material and a solvent, is applied to the surface using a nozzle apparatus. This apparatus comprises a chamber for containing the coating formulation. The chamber is connected to at least one opening in the nozzle apparatus. To apply the coating formulation, the formulation is placed into the chamber. The coating formulation is then electrically charged. Afterwards, droplets of the electrically charged coating formulation are created and dispensed through the opening and deposited onto the grounded surface to form a coating on the surface of the medical device.

In an alternative embodiment, the coating formulation, in addition to comprising a polymeric material and a solvent, can also include a biologically active material. Moreover, the nozzle apparatus, can also comprise an electrode. When such an apparatus is used, the coating formulation is electrically charged by flowing the coating formulation across the electrode.

In yet another embodiment, the medical device that is to be coated is an implantable stent. Furthermore, the polymeric material of the coating formulation is preferably stryrene-isobutylene-styrene and the solvent has a volumetric resistivity of between about $10^7$ ohm-cm and about $10^{10}$ ohm-cm.

The coatings produced by the method of the present invention are very uniform. In particular, when a coating formulation is applied to a stent having a tube-like sidewall and openings therein. The coating on both the inside surface of the stent's sidewall and that on the outside surface of the stent's sidewall are uniform. Additionally, the method of the present invention provides a much more efficient means for applying a coating formulation to the surface of a medical device. More specifically, in contrast to conventional spray-coating methods, in which only about 5% of the coating formulation that is sprayed is actually deposited on the surface, in the present method approximately up to 60% of the coating formulation that is sprayed is deposited on the surface.

Furthermore, the present method provides a more simple means of coating a medical device as compared to conventional electrostatic spray-coating because it requires fewer input sources. In particular, unlike conventional electrostatic spray-coating, in the method of the present invention a gas is not needed to atomize or form the coating formulation into droplets. Accordingly, the number of input sources to the nozzle apparatus is reduced and the method of the present invention is more simple compared to conventional electrostatic spray-coating.

Another advantage of the method of the present invention is that, because the atomizing is conducted solely by electrostatic forces, each droplet has very little kinetic energy or moves at very slow velocity. Accordingly, a spray mist of such droplets is less likely to miss the target surface.

DESCRIPTION OF THE PREFERRED EMBODIMENTS

Figure 1:
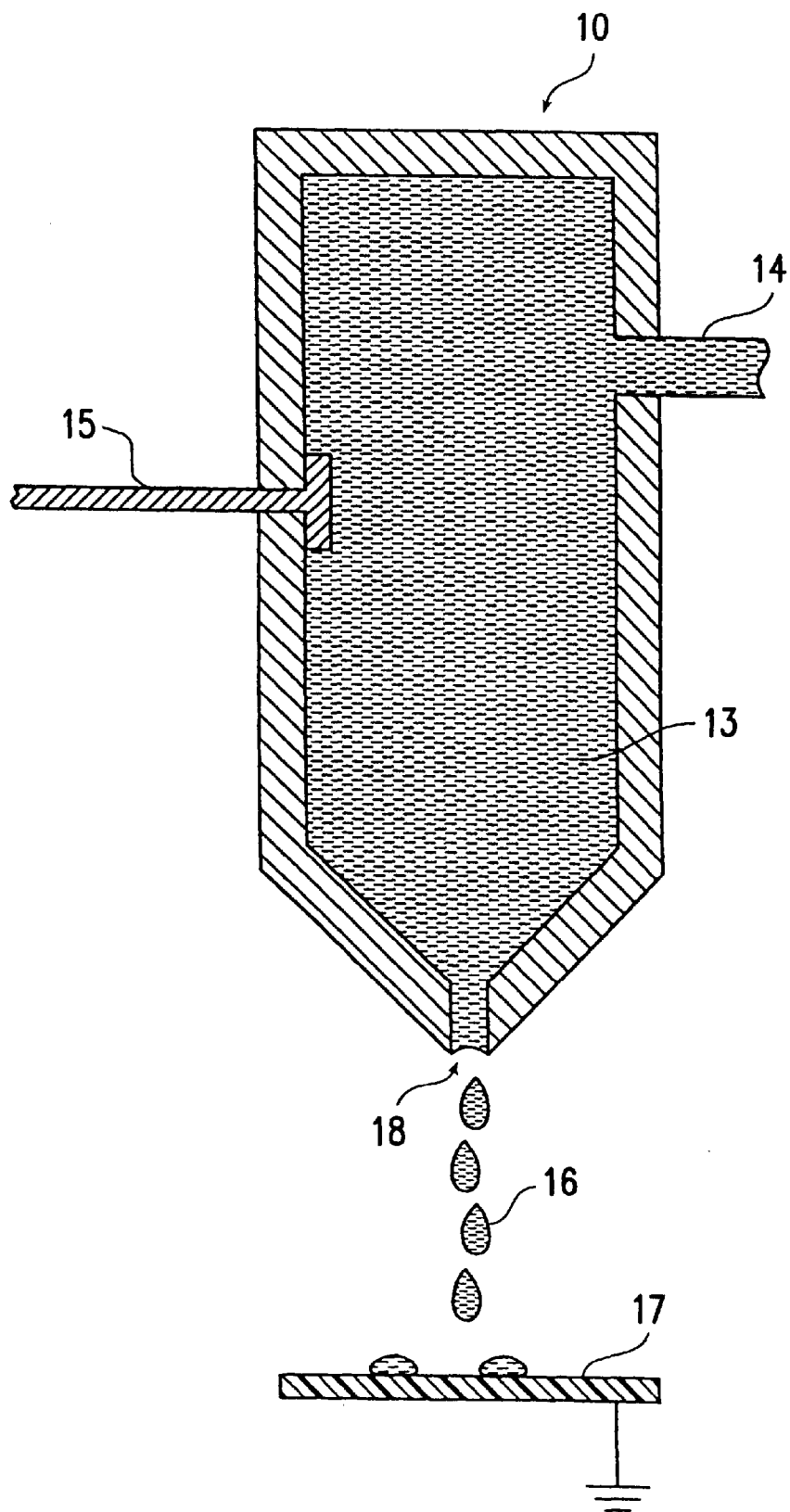
FIG. 1 depicts a cross-sectional illustration of a nozzle apparatus, having a chamber connected to an opening, that can be used in an embodiment of the present invention.

The method of the present invention can be used for coating a surface of a medical device, which has a portion for insertion or implantation into the body of a patient. The medical devices suitable for the present invention include, but are not limited to, stents, catheters, such as central venous catheters and arterial catheters, guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, extra-corporeal devices such as blood oxygenators, blood filters, hemodialysis units, hemoperfusion units or plasmapheresis units.

Medical devices which are particularly suitable for the present invention include stents, for example, vascular stents such as self-expanding stents and balloon expandable stents. Stents suitable for the present invention include any stent for medical purposes, which are known to the skilled artisan. Particularly the method of the present invention is useful for coating stents having intricate surfaces. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al. Similarly, urinary implants such as drainage catheters are also particularly appropriate for the invention.

The medical devices suitable for the present invention may be fabricated from polymeric and/or metallic materials. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646.

Coating formulations that are useful for the method of the present invention comprises a polymeric material and solvent. The polymeric material useful for forming the coating formulation should be ones that are biocompatible and avoids irritation to body tissue. Preferably the polymeric materials are biostable ones, such as polyurethanes, silicones (e.g., polysiloxanes and substituted polysiloxanes), and polyesters. Also preferable as a polymeric material is styrene-isobutylene-styrene (SIBS). Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing.

More preferably for medical devices which undergo mechanical challenges, e.g. expansion and contraction, the polymeric materials should be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating adheres better to the surface of the medical device when the device is subjected to forces, stress or mechanical challenge.

Furthermore, although the invention can be practiced by using a single type of polymer to form the coating layer(s), various combinations of polymers can be employed. The appropriate mixture of polymers can be coordinated with biologically active materials of interest to produce desired effects when coated on a medical device in accordance with the invention.

Solvents suitable for forming the coating formulation are ones which can dissolve the polymeric material into solution or form dispersions of the polymeric material in the solvent. Any solvent which does not alter or adversely impact the therapeutic properties of the biologically active material can be employed in the method of the present invention. Examples of useful solvents include tetrahydrofuran, chloroform, toluene, acetone, isooctane, 1,1,1,-trichloroethane, and mixture thereof. Preferably, chloroform or tetrahydrofuran is used as the solvent in the method of the present invention. The amount of polymeric material in the coating formulation should range from about 1 weight % to about 15 weight %. Preferably, the amount of polymeric material, in particular SIBS should be from about 1 weight % to about 3 weight %. The suitable viscosities of the coating solution range from about 1 centipoise (cps) to about 20,000 cps. The suitable volumetric resistivity of the coating solution ranges from about $1 \times 10^7$ ohm-cm to about $1 \times 10^{10}$ ohm-cm.

Coating formulations useful for the method of the present invention may also comprise a biologically active material. The term "biologically active material" encompasses therapeutic agents, such as drugs, and also genetic materials and biological materials. Suitable genetic materials include DNA or RNA, such as, without limitation, DNA/RNA encoding a useful protein and DNA/RNA intended to be inserted into a human body including viral vectors and non-viral vectors. Suitable viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Suitable non-viral vectors include artificial chromosomes and mini-chromosomes, plasmid DNA vectors (e.g., pCOR), cationic polymers (e.g. polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

Suitable biological materials include cells, yeasts, bacteria, proteins, peptides, cytokines and hormones. Examples of suitable peptides and proteins include growth factors (e.g., FGF, FGF-1, FGF-2, VEGF, Endotherial Mitogenic Growth Factors, and epidermal growth factors, transforming growth factor $\alpha$ and $\beta$, platelet derived endothelial growth factor, platelet derived growth factor, tumor necrosis factor $\alpha$, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non-genetic therapeutic agents, such as:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents, vasodilating agents, and agents which interfere with endogenous vasoactive mechanisms;

anti-oxidants, such as probucol;

antibiotic agents, such as penicillin, cefoxitin, oxacillin, tobranycin;

angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

In order to coat a surface of a medical device, the surface is first grounded by a ground line so that it becomes electrically neutral. This grounding step can be conducted in any way known to one skilled in the art.

Thereafter, the coating formulation is applied to the surface of the device using a nozzle apparatus. This apparatus should have a chamber for containing the coating formulation and an opening in fluid connection with the chamber through which the coating formulation can be dispense and deposited on the surface. The nozzle apparatus should also include or be used in conjunction with a device for electrically charging the coating formulation. For example, a conductor can be used to connect the chamber to a voltage power source. One of skill in the art would be aware of other suitable devices that can function as such a conductor.

To apply the coating formulation to the surface of the medical device, the formulation is placed into the chamber of the nozzle apparatus. The coating formulation can be pumped into the chamber. When the coating formulation is placed into the chamber, it contacts the conductor, such as a high-voltage DC electrode, and becomes charged. Once the coating formulation in the chamber is charged, it carries the same charge as the conductor. As a result the formulation and conductor repel each other. This repulsive force discharges the coating formulation through the opening of the nozzle to create streams of droplets. Therefore, in the method of the present invention, no additional gas source is required for atomization of the coating formulation. Accordingly, a cloud of highly charged, highly uniform-sized droplets can be formed.

Since the droplets that are formed carry a charge, when they are deposited on the grounded surface of the medical device, they will be guided by their electrostatic attraction to the grounded and hence electrically neutral surface. Because the areas of the surface that are not covered with coating formulation are best grounded, they will more strongly attract newly-arriving droplets than areas that have already been coated. Also, since the droplets carry the same electrical charge, they will repel each other. This repulsion causes the droplets arriving at the surface to avoid the areas where other droplets have already been deposited and instead land on areas of the surface that have not been coated. In this way, an inherently uniform coating is formed. With respect to a stent having openings in its sidewall, this method allows those areas of the inside and outside surfaces of the stent's sidewall to be uniformly coated even though the inside surface may be obstructed by the outside surface of the stent's sidewall.

One example of a suitable nozzle apparatus that can be used in the method of the invention is an apparatus for electrohydrodynamic spray-coating that is disclosed in U.S. Pat. No. 4,749,125, to Escallon et al. This apparatus has a metal shim that is placed within the nozzle apparatus to define a plurality of nozzle openings. The metal shim is also connected to a voltage source which allows for the formation of electrically charged droplets of coating formulation.

FIG. 1 is a cross-sectional illustration of a nozzle apparatus 10 useful for an embodiment of the method of the present invention. The nozzle apparatus 10 has a chamber 13 to contain the coating formulation, which is supplied to the chamber 13 through a tube 14 connected to a coating formulation reservoir (not shown). The coating formulation contained in the chamber 13 is electrically charged by a conductor 15 connected to a voltage power source (not shown). A surface of a medical device 17 is placed at an appropriate distance from the nozzle apparatus 10 and grounded. The electrically charged coating formulation is atomized at or near the opening 18 of the nozzle apparatus and becomes electrically charged droplets 16. The droplets 16, which carry a like charge, repel each other and the conductor 15 and are attracted to the grounded surface of the medical device 17 to form an even coating on the surface of the medical device 17.

Figure 2:
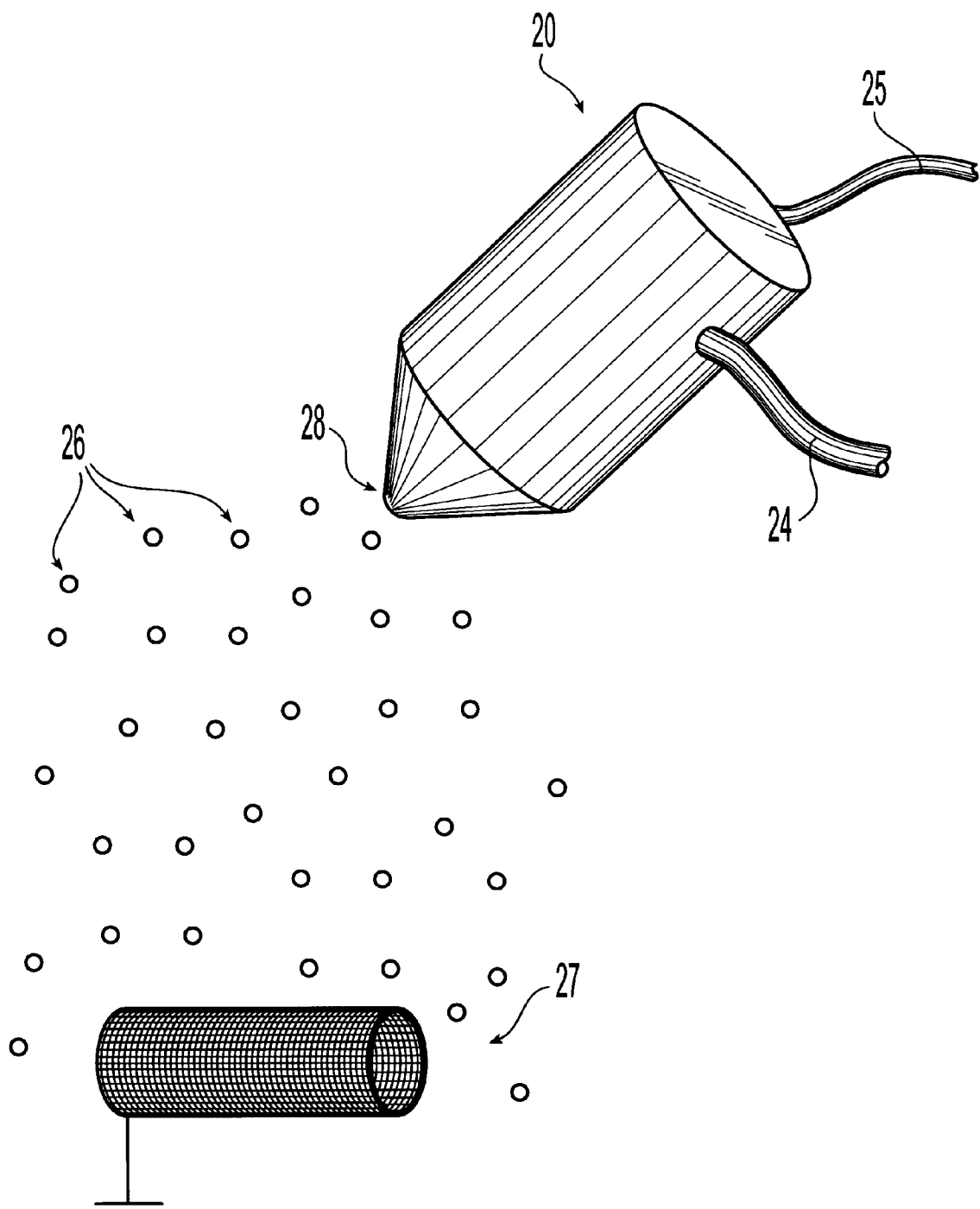
FIG. 2 depicts a perspective view of a nozzle apparatus that is useful in another embodiment of the method of the present invention.

FIG. 2 is a perspective view of a nozzle apparatus 20 that is useful in another embodiment of the present invention. The nozzle apparatus 20 has a tube 24 that is in fluid connection with a coating formulation reservoir (not shown) and a conductor 25 connected to a voltage power supply (not shown). The conductor 25 electrically charges the coating formulation in the reservoir (not shown) of the nozzle apparatus 20. The nozzle apparatus 20 atomizes an electrically charged coating formulation at or near the opening 28 of the nozzle apparatus and creates a cloud of charged droplets 26 of the coating formulation. The droplets 26 repel each other and are attracted to the grounded surface of a wire stent 27. Because the charged droplets are attracted to uncoated areas of the stent, the inside surface of the stent's sidewall, which is obstructed in part by the outside surface of the stent's sidewall is uniformly coated as compared to the outside surface of the stent's sidewall, i.e. both the inside and outside surfaces contain approximately the same amount of coating formulation per unit area.

Although the nozzle apparatus can be made of any insulative material, such as a polyamide, preferably, it is made of ceramics. Also, preferably, the flow rate of the coating formulation at the opening of the nozzle apparatus is at about 0.02 milliliter per minute (ml/min) to about 0.1 ml/min. Additionally, the amount of voltage used to charge the coating formulation preferably ranges from about 8 kV to 20 kV and the current used preferably ranges from about 5 microamps to about 40 microamps. The method of this invention may be conducted at room temperature.

The nozzle apparatus is preferably placed at about 50 mm to about 120 mm away from the surface of the medical device that is to be coated. Furthermore, although conventional spray-coating methods require that the medical device be placed in a rotating fixture to facilitate the coating of the device's surface, in the method of the present invention, the medical device does not have to be rotated in order for its surface to be coated. The device may be placed into a fixture. Any kind of fixtures used for conventional spray coating can be used. For example, when the entire surface of a vascular stent is to be coated, the ends of the stent are fastened, such as by alligator clips. However, for the method of the present invention, the fastened stent does not have to be rotated as for the conventional spray coating methods. Also, more than one medical device can be coated when they are placed into such a fixture. Also, more than one nozzle apparatus can be used at the same time for the method of the present invention.

Using the method of the present invention, a very thin and even coating can be achieved. For example, the thickness of the coating that is formed by using the method of the present invention can even be as thin as about 10 µm.

When the surface of the device is coated with more than one cycle of spraycoating, different coating formulations may be used in each of the spray-coating cycles. For instance, the first coating formulation that is applied may contain a first polymeric material and a first solvent and the second coating formulation that is applied may contain a second polymeric material, a second solvent as well as a biologically active material.

After application of the coating formulation to the surface of the medical device, the coating can be cured to produce a polymer matrix and to evaporate the solvent. Curing is defined as the process of converting the elastomeric or polymeric material into the finished or useful state by the application of heat and/or chemical agents which induce physico-chemical changes. The applicable time and temperature for curing are determined by the particular polymer involved and particular biologically active material used, if any. Certain polymers, such as silicone and urethane prepolymers, can be cured at relatively low temperatures, (e.g. room temperature) in what is known as a room temperature vulcanization (RTV) process. Unlike the polyurethane thermoplastic elastomers, more typically, the curing/evaporation process involves higher temperatures so that the coated device is heated in an oven. Typically, the heating occurs at approximately 90° C. or higher for approximately 1 to 16 hours when silicone is used. For certain coatings such as ones containing dexamethasone, the heating may occur at temperatures as high as 150° C. The time and temperature of heating will of course vary with the particular polymer, biologically active material, solvents and/or crosslinkers used. One of skill in the art is aware of the necessary adjustments to these parameters. Also, if there are more than one coating layer, the devices may be cured after all or some of the coating layers have been applied.

Moreover, after the medical devices are coated, they should be sterilized. Methods of sterilization are known in the art. For example, the devices can be sterilized by exposure to gamma radiation at 2.5–3.5 Mrad or by exposure to ethylene oxide. For sterilization, exposure to gamma radiation is a preferred method, particularly for heparin containing coatings. However, for certain medical devices which undergo mechanical challenges, such as expandable vascular stents, it has been found that subjecting such coated devices to gamma radiation sterilization may reduce their ability to expand. To avoid such reduction, the gas plasma treatment described above should be applied to the coated devices as a pretreatment for gamma sterilization.

EXAMPLE

A 7 cell Conformer Stent having a length of 16 mm was placed in a fixture and grounded. A coating formulation containing 1 weight % styrene-isobutylene-styrene in 99 weight % chloroform was prepared. This formulation was placed into the chamber of an electrohydrodynamic nozzle apparatus. This apparatus is commercially available from Terronic Development Co.

The formulation in the chamber of the apparatus was electrically charged and atomized using a voltage power source connected to the apparatus that was set at 12 kV and 10–15 micro amps current. The flow rate of the coating formulation at the nozzle opening was about 0.05 ml/min.

The apparatus was placed above the stent such that the distance between its nozzle opening and the stent was about 85 mm. The stent was exposed to the atomized droplets of the coating formulation for about 4 minutes.

Figure 3:
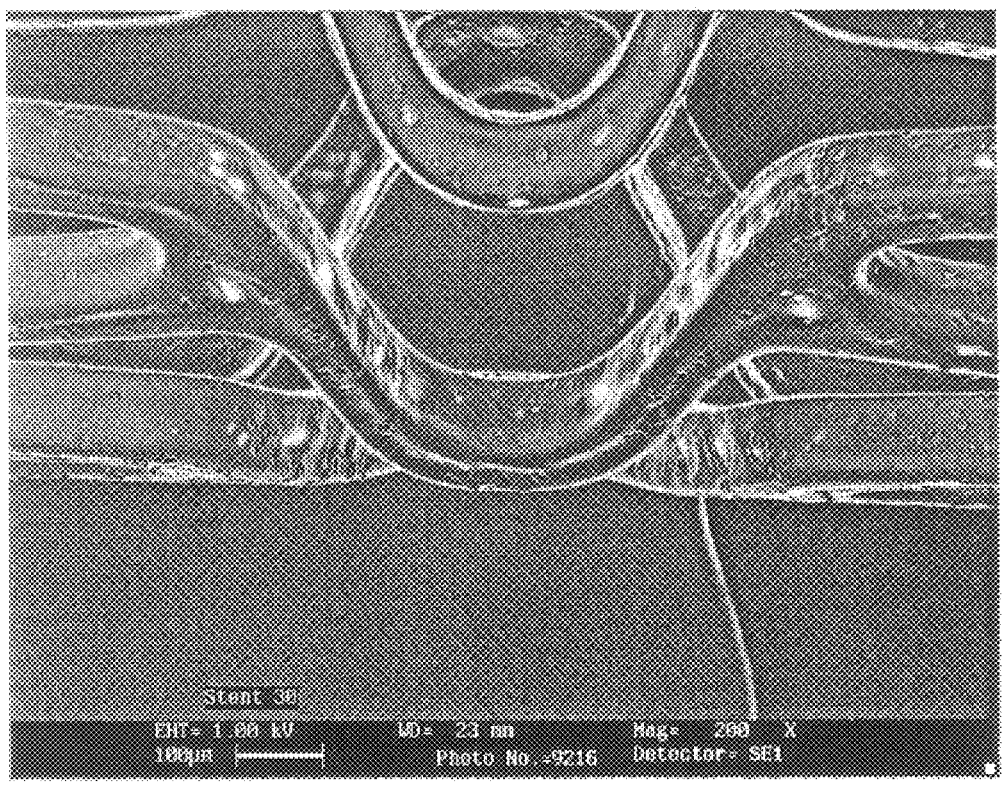
FIG. 3 is a scanning electron micrograph (SEM) (at 200× magnification) of a stent coated by the method of the present invention.
Figure 4:
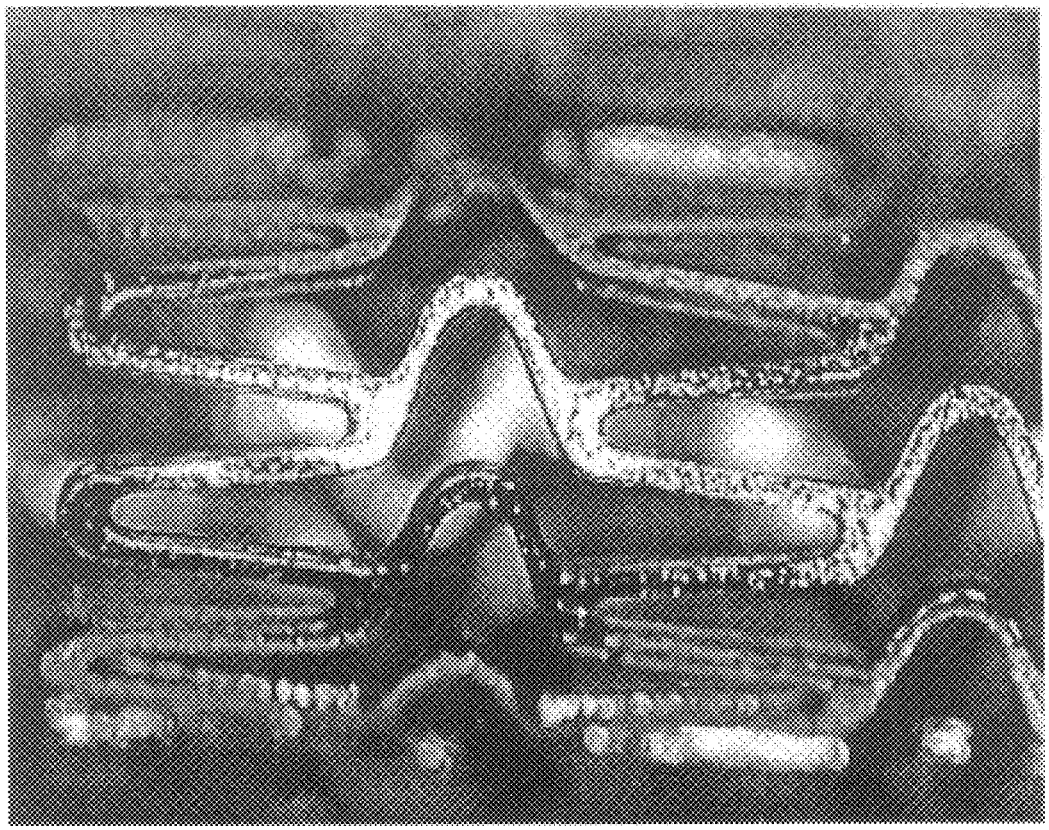
FIG. 4 is an ordinary micrograph (at about 30–40× magnification) of the same stent as shown in FIG. 3.

The stent was heated to dry substantially all of the solvent. The weight of the coating was 1.0 mg, and the average thickness was about 20 µm. The coated stent was also examined by a scanning electron microscope (SEM) and an ordinary microscope, and the micrographs are shown in FIGS. 3 and 4. FIG. 3 is a SEM at 200×magnification, and FIG. 4 is an ordinary micrograph at about 30–40× magnification. These figures show that the coating is very even without any cross webbing or bare spots.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

I claim:

1. A method for coating at least a portion of a medical device, wherein the portion has a surface adapted for exposure to body tissue of a patient, the method comprising:
   (a) grounding the surface; and
   (b) applying to the surface a coating formulation comprising a polymeric material comprising styrene-isobutylene-styrene and a solvent, said step of applying comprising the steps of
      (1) providing a nozzle apparatus comprising a chamber connected to at least one opening for dispensing the coating formulation;
      (2) placing the coating formulation into the chamber;
      (3) electrically charging the coating formulation;
      (4) creating droplets of the electrically charged coating formulation; and
      (5) depositing the droplets of coating formulation onto the grounded surface to form a coating on the surface.

2. The method of claim 1 wherein the nozzle apparatus further comprises a conductor that connects the chamber to a voltage power source.

3. The method of claim 2 in which the conductor is an electrode and the coating formulation is electrically charged by flowing the coating formulation across the electrode.

4. The method of claim 1, wherein step (b) is repeated at least one time.

5. The method of claim 4, wherein step (b) is repeated using a second coating formulation.

6. The method of claim 1, wherein the coating formulation further comprises a biologically active material.

7. The method of claim 1, wherein the droplets of coating formulation are deposited at a flow rate of about 0.02 ml/min to about 0.1 ml/min.

8. The method of claim 1, wherein the coating formulation has a volumetric resistivity of from about $10^7$ ohm-cm to about $10^{10}$ ohm-cm.

9. The method of claim 1, wherein the coating formulation has a viscosity of from about 1 cps to about 20,000 cps.

10. The method of claim 1, wherein the coating formulation is electrically charged by a voltage power source having a voltage of about 8 kV to about 12 kV and a current of about microamp 5 to about 40 microamp.

11. The method of claim 1, wherein the solvent is selected from a group consisting of tetrahydrofuran, chloroform, toluene, acetone, isooctane, 1,1,1-trichloroethane and mixtures thereof.

12. The method of claim 1, wherein the solvent is chloroform.

13. The method of claim 1, wherein the polymeric material is about 1 to about 15 weight % of the coating formulation.

14. The method of claim 6, wherein the polymeric material has a melting point that is lower than the decomposition temperature of the biologically active material.

15. A method for coating at least a portion of a medical device, wherein the portion has a surface adapted for exposure to body tissue of a patient, the method comprising:

(a) grounding the surface; and (b) applying to the surface a coating formulation comprising a polymeric material comprising styrene-isobutylene-styrene, a biologically active material and a solvent, said step of applying comprising the steps of (1) providing a nozzle apparatus comprising an electrode and a chamber connected to at least one opening for dispensing the coating formulation;

(2) placing the coating formulation into the chamber;

(3) electrically charging the coating formulation by flowing the coating formulation across the electrode;

(4) creating droplets of the electrically charged coating formulation; and (5) deposition the droplets of coating formulation onto the grounded surface to form a coating on the surface.

16. A method for coating a surface of an implantable stent, the method comprising:

(a) grounding the surface; and (b) applying a coating formulation, which comprises a polymeric material comprising styrene-isobutylene-styrene, a biologically active material and a solvent to the surface, using a nozzle apparatus by:

(1) providing the nozzle apparatus comprising a chamber connected to at least one opening for dispensing the coating formulation;

(2) placing the coating formulation into the chamber;

(3) electrically charging the coating formulation;

(4) creating droplets of the electrically charged coating formulation; and (5) depositing the droplets of coating formulation onto the grounded surface to form a coating on the surface.

* * * * *